United States Patent
Sawanoi et al.

(10) Patent No.: US 9,364,156 B2
(45) Date of Patent: Jun. 14, 2016

(54) BLOOD PRESSURE MEASUREMENT DEVICE AND CONTROL METHOD FOR BLOOD PRESSURE MEASUREMENT DEVICE

(71) Applicant: OMRON HEALTHCARE Co., Ltd., Kyoto (JP)

(72) Inventors: Yukiya Sawanoi, Kyoto (JP); Kenji Fujii, Kyoto (JP); Naomi Matsumura, Kyoto (JP); Reiji Fujita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 884 days.

(21) Appl. No.: 13/628,696

(22) Filed: Sep. 27, 2012

(65) Prior Publication Data
US 2013/0023778 A1    Jan. 24, 2013

Related U.S. Application Data

(63) Continuation of application No. PCT/JP2011/052634, filed on Feb. 8, 2011.

(30) Foreign Application Priority Data

Mar. 30, 2010 (JP) .................................. 2010-077939

(51) Int. Cl.
*A61B 5/02* (2006.01)
*A61B 5/0225* (2006.01)
*A61B 5/00* (2006.01)

(52) U.S. Cl.
CPC ........... *A61B 5/02255* (2013.01); *A61B 5/6824* (2013.01)

(58) Field of Classification Search
CPC ........... A61B 5/02116; A61B 5/02438; A61B 5/7239; A61B 5/021; A61B 5/022; A61B 5/02255; A61B 5/02225
See application file for complete search history.

(56) References Cited

U.S. PATENT DOCUMENTS

| 8,715,197 B2 * | 5/2014 | Sawanoi ............. A61B 5/0225 600/490 |
| 2009/0312652 A1 | 12/2009 | Yamakoshi et al. |

FOREIGN PATENT DOCUMENTS

| JP | 54-050175 A | 4/1979 |
| JP | 59-156325 A | 9/1984 |

(Continued)

OTHER PUBLICATIONS

Machine Translation of JP-8-581.*

(Continued)

*Primary Examiner* — Michael Kahelin
*Assistant Examiner* — Tho Tran
(74) *Attorney, Agent, or Firm* — Osha Liang LLP

(57) ABSTRACT

A blood pressure measurement device includes a cuff, inflation/deflation unit, pressure detection unit, volume detection unit, and control unit. The control unit determines values of an arterial volume signal detected by the volume detection unit, changes a prescribed control target value from the determined value at a time of diastolic blood pressure to a vicinity of the value at the time of systolic blood pressure during a rise time, changes the prescribed control target value from the determined value at the time of systolic blood pressure to a vicinity of the value at the time of diastolic pressure during a fall time, and adjusts the pressure of the cuff by controlling the inflation/deflation unit such that the volume indicated by the arterial volume signal detected by the volume detection unit matches the prescribed control target value. Thus, by applying a control target value, blood pressure can be measured.

4 Claims, 8 Drawing Sheets

(56) References Cited

FOREIGN PATENT DOCUMENTS

| | | |
|---|---|---|
| JP | 08-000581 A | 1/1996 |
| JP | 2009-285028 A | 12/2009 |
| JP | 2009-285029 A | 12/2009 |
| JP | 2010-051659 A | 3/2010 |
| WO | 2008/015921 A1 | 2/2008 |
| WO | 2010/024129 A1 | 3/2010 |

OTHER PUBLICATIONS

International Search Report issued in corresponding International Application No. PCT/JP2011/052634 dated Mar. 15, 2011 and English translation thereof (4 pages).

Patent Abstracts of Japan, Publication No. 08-000581, Published on Jan. 9, 1996, 1 page.

Patent Abstracts of Japan, Publication No. 2010-051659, Published on Mar. 11, 2010, 1 page.

Patent Abstracts of Japan, Publication No. 2009-285029, Published on Dec. 10, 2009, 1 page.

Patent Abstracts of Japan, Publication No. 2009-285028, Published on Dec. 10, 2009, 1 page.

Office Action issued in counterpart Chinese Patent Application No. 201180018033.3 dated Mar. 11, 2014 (14 pages).

* cited by examiner

BLOOD PRESSURE MEASUREMENT DEVICE AND CONTROL METHOD FOR BLOOD PRESSURE MEASUREMENT DEVICE

TECHNICAL FIELD

The present invention relates to a blood pressure measurement device and a control method for the blood pressure measurement device, and more particularly to a blood pressure measurement device that measures blood pressure using a volume compensation method and a control method for the blood pressure measurement device.

BACKGROUND ART

With a conventional electronic sphygmomanometer, an arm belt (cuff) is wrapped around a measurement site, and during a process in which the cuff (cuff pressure) is inflated to a higher pressure than systolic blood pressure and thereafter gradually deflated, the pulse produced by an artery is detected with a pressure sensor via the cuff, and systolic blood pressure and diastolic blood pressure are determined using the cuff pressure and the magnitude (pulse wave amplitude) of the pulse at that time (oscillometric method).

In contrast, a volume compensation type sphygmomanometer configured to continuously measure blood pressure per heartbeat in a non-invasive manner has been developed (see JP 54-50175A (hereinafter "Patent Literature 1")). The volume compensation method is a method in which compression pressure (cuff pressure) is equalized with intra-arterial pressure, that is, blood pressure, by compressing an artery with a cuff from outside the body and keeping the volume of the pulsating artery uniform per unit length, and continuous blood pressure values are obtained by detecting the cuff pressure when this state is maintained.

By keeping the intra-arterial pressure and the cuff pressure on the artery constantly in equilibrium, the arterial wall is unloaded (i.e., natural state in which pressure is not exerted). In view of this, detecting the volume value (control target value) when the artery is in an unloaded state and maintaining this state (servo control) are two important points. In particular, because the accuracy of the control target value greatly influences blood pressure measurement accuracy, determining the control target value is very important.

A method of determining the control target value has been invented that involves detecting the maximum point of an arterial volume change signal (AC component of volume pulse wave) obtained from a photoelectric volume pulse wave or an impedance pulse wave while gradually compressing an artery using a cuff, and taking an arterial volume value (DC component of volume pulse wave) at that time as the control target value (see JP 59-156325A (hereinafter "Patent Literature 2")). With an electronic sphygmomanometer using the volume compensation method of Patent Literature 2, a fixed control target value is used for the entire range of control cuff pressures.

However, the change in the DC component of the volume pulse wave under the influence of the deformation of body tissue around an artery in the process of compressing the artery is in actual fact greater than the change in arterial volume. Thus, the blood pressure may only be able to be measured on a finger where the deformation of body tissue is limited, and the measured difference (pulse pressure) between systolic blood pressure and diastolic blood pressure may be smaller than the actual blood pressure value.

A method of determining a control target value that incorporates the influence of the deformation of body tissue has been invented (see JP 8-581A (hereinafter "Patent Literature 3")). In this invention, diastolic blood pressure and systolic blood pressure are calculated using an oscillometric method during the process of gradually compressing an artery, and the arterial volume values at these two points are detected. These two points serve as the control target values for diastolic blood pressure and systolic blood pressure. Interpolating these two points with an arbitrary curve enables control target values that incorporate the influence of the deformation of body tissue at arbitrary points within one heartbeat to be determined. Using control target values determined in this way enables measurement error that arises in the case where a fixed control target value is used to be eliminated.

Patent Literature 1: JP 54-50175A
Patent Literature 2: JP 59-156325A
Patent Literature 3: JP 8-581A

SUMMARY OF INVENTION

However, in the invention of Patent Literature 3, even though a method of determining a control target value that incorporates the influence of the deformation of body tissue is demonstrated, a method of actually using this control target value is not demonstrated. Thus, a control target value that incorporates the influence of the deformation of body tissue cannot be applied in an actual volume compensation type sphygmomanometer.

Therefore, one or more embodiments of the present invention provide a blood pressure measurement device capable of measuring blood pressure by applying a control target value that incorporates the influence of the deformation of body tissue using a volume compensation method, and a control method for the blood pressure measurement device.

According to one or more embodiments of the present invention, a blood pressure measurement device is a device for measuring blood pressure in accordance with a volume compensation method that includes a cuff that compresses an artery of a blood pressure measurement site in a case where the device is fitted on the measurement site, an inflation/deflation unit that increases and decreases a pressure inside the cuff, a pressure detection unit that detects a cuff pressure, which is the pressure inside the cuff, a volume detection unit that detects an arterial volume signal indicating a volume of the artery per unit length, and a control unit, the control unit including a pressure control unit that adjusts the pressure of the cuff by controlling the inflation/deflation unit, such that the volume indicated by the arterial volume signal detected by the volume detection unit matches a prescribed control target value, and an extraction unit that extracts, as a blood pressure of a subject, the cuff pressure detected by the pressure detection unit when a prescribed condition that judges that the volume matches the prescribed control target value as a result of adjustment by the pressure control unit is satisfied.

The control unit further includes a determination unit that respectively determines, as a value at a time of diastolic blood pressure and a value at a time of systolic blood pressure, values of the arterial volume signal detected by the volume detection unit when the cuff pressure matches a diastolic blood pressure and a systolic blood pressure calculated with a prescribed method, a change point detection unit that detects a rising point where the volume indicated by the arterial volume signal detected by the volume detection unit starts to increase and a falling point where the volume starts to decrease, and a change unit that changes the prescribed control target value from the value at the time of diastolic blood pressure determined by the determination unit to a vicinity of the value at the time of systolic blood pressure, during a rise time from when the rising point is detected by the change point detection unit until when the falling point is detected, and changes the prescribed control target value from the value at the time of systolic blood pressure determined by the determination unit to a vicinity of the value at the time of diastolic blood pressure, during a fall time from when the falling point is detected until when the rising point is detected.

According to one or more embodiments of the present invention, the change unit, during the rise time, changes the prescribed control target value in accordance with a value output when a waveform that is stepped from the value at the time of diastolic blood pressure determined by the determination unit to the value at the time of systolic blood pressure is input to a low-pass filter, and, during the fall time, changes the prescribed control target value in accordance with a value output when a waveform that is stepped from the value at the time of systolic blood pressure to the value at the time of diastolic blood pressure is input to the low-pass filter.

According to one or more embodiments of the present invention, a time constant of the low-pass filter is set longer for the fall time than for the rise time.

According to one or more embodiments of the present invention, a method of controlling a blood pressure measurement device is a control method for a blood pressure measurement device that is for measuring blood pressure in accordance with a volume compensation method. The blood pressure measurement device has a cuff that compresses an artery of a blood pressure measurement site with the pressure of an internal liquid or gas in a case where the device is fitted on the measurement site, an inflation/deflation unit that increases and decreases a pressure inside the cuff, a pressure detection unit that detects a cuff pressure, which is the pressure inside the cuff, a volume detection unit that detects an arterial volume signal indicating a volume of the artery per unit length, and a control unit.

According to one or more embodiments of the present invention, the control method for the blood pressure measurement device includes a step of the control unit respectively determining, as a value at a time of diastolic blood pressure and a value at a time of systolic blood pressure, values of the arterial volume signal detected by the volume detection unit when the cuff pressure matches a diastolic blood pressure and a systolic blood pressure calculated with a prescribed method, a step of the control unit detecting a rising point where the volume indicated by the arterial volume signal detected by the volume detection unit starts to increase and a falling point where the volume starts to decrease, a step of the control unit changing the prescribed control target value from the determined value at the time of diastolic blood pressure to a vicinity of the value at the time of systolic blood pressure, during a rise time from when the rising point is detected until when the falling point is detected, and changing the prescribed control target value from the determined value at the time of systolic blood pressure to a vicinity of the value at the time of diastolic blood pressure, during a fall time from when the falling point is detected until when the rising point is detected, a step of the control unit adjusting the pressure of the cuff by controlling the inflation/deflation unit, such that the volume indicated by the arterial volume signal detected by the volume detection unit matches a prescribed control target value, and a step of the control unit extracting, as a blood pressure of a subject, the cuff pressure detected by the pressure detection unit when a prescribed condition for judging that the volume matches the prescribed control target value as a result of adjustment of the pressure of the cuff is satisfied.

According to one or more embodiments of the present invention, a blood pressure measurement device respectively determines the values of an arterial volume signal detected by a volume detection unit when cuff pressure matches diastolic blood pressure and systolic blood pressure calculated by a prescribed method as a value at the time of diastolic blood pressure and a value at the time of systolic blood pressure, detects a rising point and a falling point where the volume indicated by the arterial volume signal detected by the volume detection unit respectively starts to increase and decrease, changes a prescribed control target value in a range from the determined value at the time of diastolic blood pressure to a vicinity of the determined value at the time of systolic blood pressure, during a rise time from when the rising point is detected until when the falling point is detected, and changes the prescribed control target value in a range from the determined value at the time of systolic blood pressure to a vicinity of the determined value at the time of diastolic blood pressure, during a fall time from when the falling point is detected until when the rising point is detected.

The blood pressure measurement device is thus able to obtain the blood pressure of a subject while changing the control target value to a value depending on a value approximating the blood pressure value at respective timings. As a result, a blood pressure measurement device capable of measuring blood pressure by applying a control target value that incorporates the influence of the deformation of body tissue using a volume compensation method and a control method for the blood pressure measurement device can be provided.

DETAILED DESCRIPTION OF INVENTION

Figure 1:
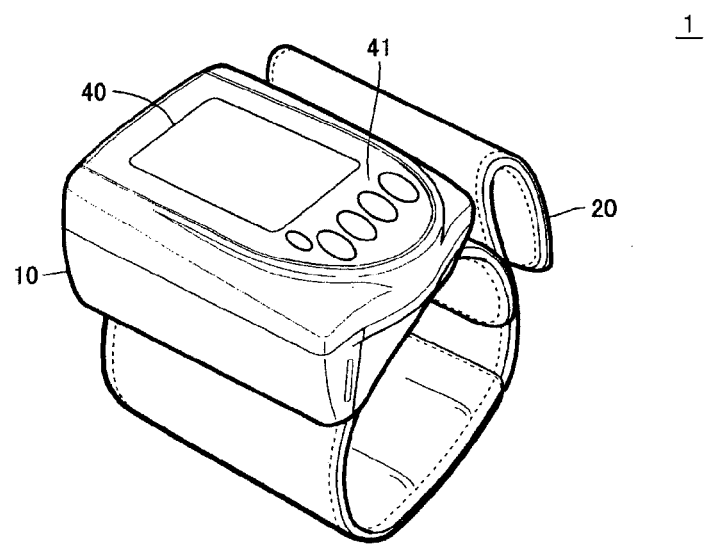
FIG. 1 is an external perspective view of an electronic sphygmomanometer according to an embodiment of the present invention.

Hereinafter, an embodiment of this invention will be described in detail with reference to drawings. Note that the same reference signs are given to the same or equivalent portions in the drawings, and description thereof will not be repeated.

An electronic sphygmomanometer 1 according to the present embodiment measures blood pressure continuously using a volume compensation method. The electronic sphygmomanometer 1 applies external pressure to an artery from outside the body using a cuff, and performs servo control using a determined optimal servo gain, such that the external pressure, or cuff pressure, on the body is constantly in equilibrium with an intra-arterial pressure, or blood pressure. In other words, the electronic sphygmomanometer 1 fine tunes the cuff pressure such that an arterial wall is maintained in an unloaded state, and measures blood pressure continuously by measuring the cuff pressure at that time (unloaded state).

FIG. 1 is an external perspective view of the electronic sphygmomanometer 1 according to an embodiment of the present invention. Referring to FIG. 1, the electronic sphygmomanometer 1 is provided with a main body 10 and a cuff 20 that can be wrapped around the limbs of a subject. The main body 10 is attached to the cuff 20. A display unit 40 constituted by liquid crystal, for example, and an operation unit 41 for receiving instructions from a user (subject) are disposed on the surface of the main body 10. The operation unit 41 includes a plurality of switches.

In the present embodiment, "limbs" denotes the upper limbs and lower limbs. In other words, the limbs include the region from the wrist to the top of the arm, and the region from the ankle to the top of the leg. In the following description, the cuff 20 is fitted on the wrist of the subject.

Note that while a configuration in which the main body 10 of the electronic sphygmomanometer 1 in the present embodiment is attached to the cuff 20, as shown in FIG. 1, is described as an example, an embodiment is possible in which the main body 10 and the cuff 20 are connected by an air tube (air tube 31 in FIG. 3 mentioned below), such as employed with an upper arm sphygmomanometer.

Figure 2:
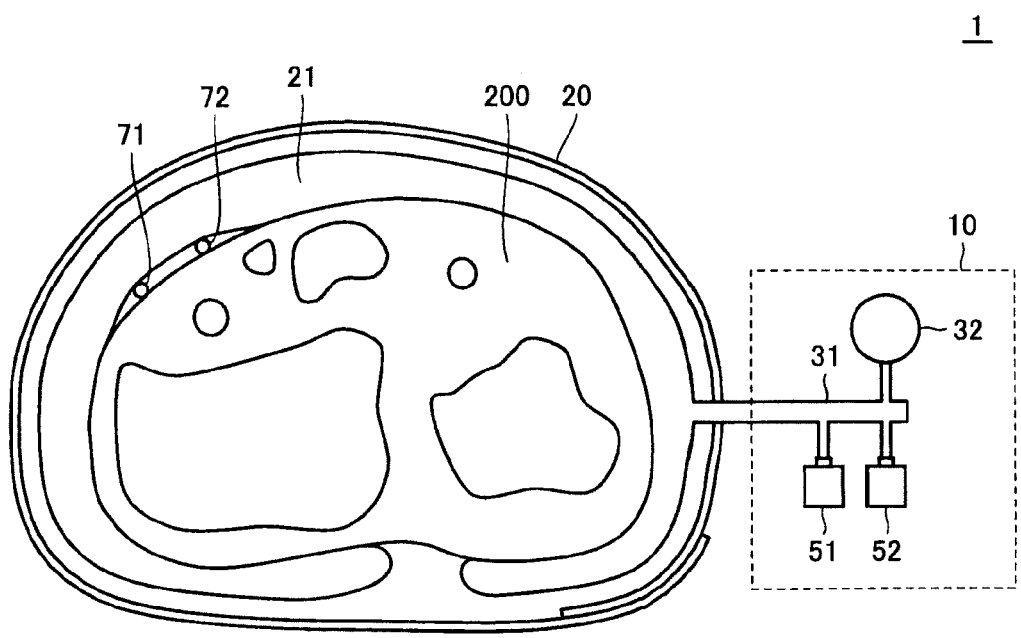
FIG. 2 is a diagram representing a concept of controlling cuff pressure for measuring blood pressure in an electronic sphygmomanometer according to an embodiment of the present invention.

FIG. 2 is a diagram representing the concept of controlling cuff pressure for measuring blood pressure in the electronic sphygmomanometer 1 according to an embodiment of the present invention. In FIG. 2, the cuff 20 is shown being fitted on a wrist 200 of a subject.

Referring to FIG. 2, a cuff pressure adjustment mechanism including a pump 51 and an exhaust valve (hereinafter, simply "valve") 52 is disposed on the main body 10.

An air system 30 including the pump 51, the valve 52 and a pressure sensor 32 for detecting the pressure (cuff pressure) in an air bag 21 contained in the cuff 20 is connected to the air bag 21 via the air tube 31.

A light emitting element 71 and a light receiving element 72 are disposed at a prescribed interval on the inner side of the air bag 21. Although the light emitting element 71 and the light receiving element 72 in the present embodiment are arranged around the wrist 200 when the cuff 20 is fitted, the disposition thereof is not limited to this example.

Also, although the air bag 21 is included in the cuff 20, the fluid supplied to the cuff 20 is not limited to air, and may be a liquid or gel, for example. Nor is the substance limited to a fluid, and may be uniform small particles such as micro beads.

Figure 3:
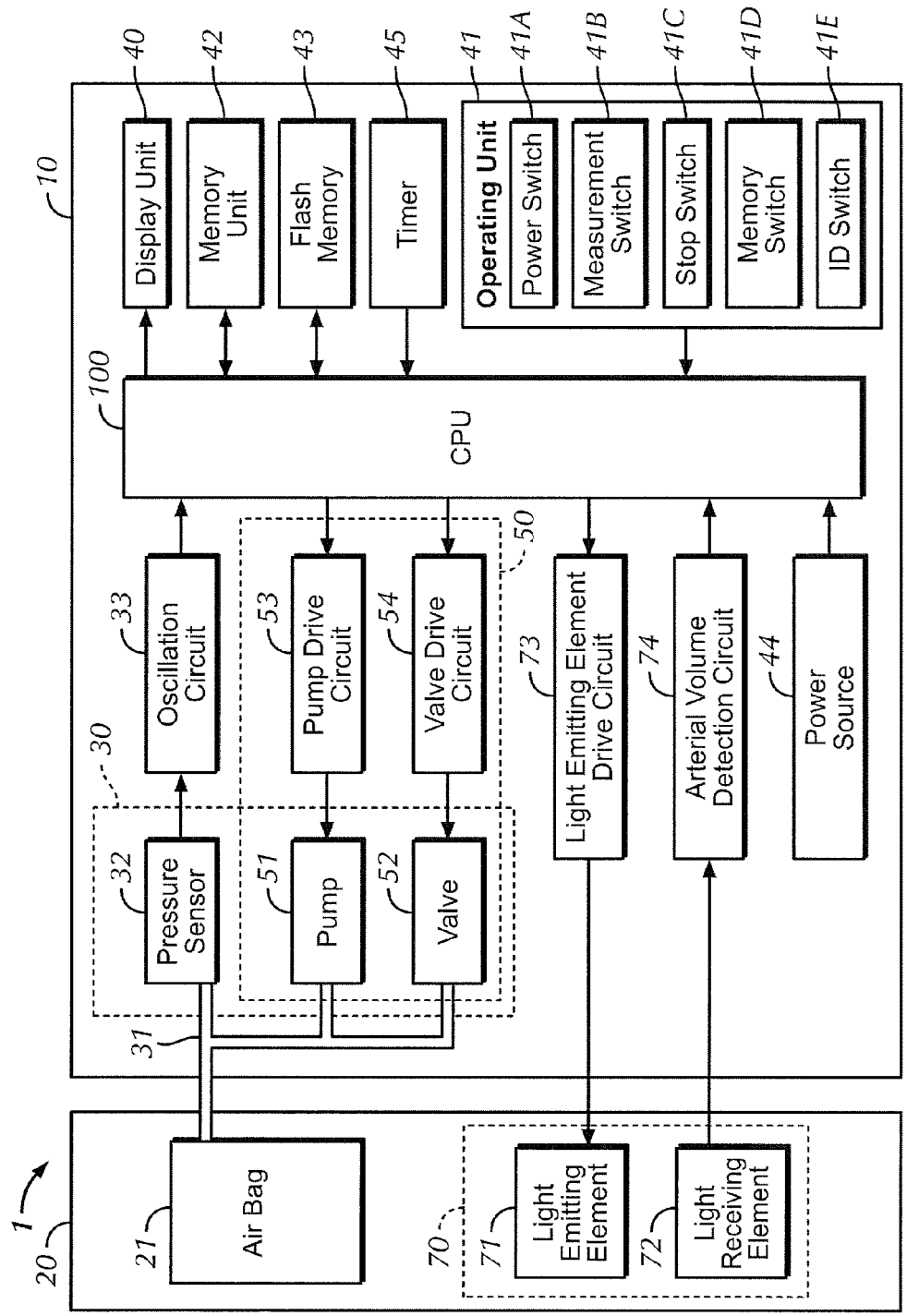
FIG. 3 is a block diagram representing a hardware configuration of an electronic sphygmomanometer according to an embodiment of the present invention.

FIG. 3 is a block diagram showing a hardware configuration of the electronic sphygmomanometer 1 according to an embodiment of the present invention. Referring to FIG. 3, the cuff 20 of the electronic sphygmomanometer 1 includes the air bag 21 and an arterial volume sensor 70.

The arterial volume sensor 70 is a sensor for detecting the volume of an artery at the blood pressure measurement site of the subject, and is constituted by a photoelectric sensor having the abovementioned light emitting element 71 (e.g., light emitting diode) and light receiving element 72 (e.g., phototransistor). The light emitting element 71 irradiates light toward an artery, and the light receiving element 72 receives light irradiated by the light emitting element 71 that has been transmitted or reflected by the artery.

Note that the arterial volume sensor 70 need only be able to detect the volume of an artery, and may be configured to detect the volume of an artery using an impedance sensor (impedance plethysmograph). In this case, the light emitting element 71 and the light receiving element 72 are replaced by a plurality of electrodes (pair of electrodes for applying current and a pair of electrodes for detecting voltage) for detecting the impedance of a site that includes an artery.

In addition to the abovementioned display unit 40 and operation unit 41, the main body 10 includes a central processing unit (CPU) 100 for performing centralized control of the various units and performing various arithmetic processing, a memory unit 42 for storing programs for causing the CPU 100 to perform prescribed operations and various data, a nonvolatile memory for storing measured blood pressure data, such as a flash memory 43, for example, a power source 44 for supplying power to the various units via the CPU 100, and a timer 45 that clocks the current time and outputs time data to the CPU 100.

The operation unit 41 has a power switch 41A for receiving input of an instruction for turning power on/off, a measurement switch 41B for receiving a measurement start instruction, a stop switch 41C for receiving a measurement stop instruction, a memory switch 41D for receiving an instruction to read out information such as blood pressure and the like recorded in the flash memory 43, and an ID switch 41E that is operated in order to input identification (ID) information for identifying the subject.

The main body 10 further includes the abovementioned air system 30, a cuff pressure adjustment mechanism 50, an oscillation circuit 33, a light emitting element drive circuit 73, and an arterial volume detection circuit 74.

The adjustment mechanism 50 has a pump drive circuit 53 and a valve drive circuit 54, in addition to the pump 51 and the valve 52.

The pump 51 supplies air to the air bag 21, in order to increase the cuff pressure. The valve 52 is opened or closed in order to discharge air from or enclose air in the air bag 21. The pump drive circuit 53 controls the drive of the pump 51 based on a control signal provided from the CPU 100. The valve drive circuit 54 controls opening and closing of the valve 52 based on a control signal provided from the CPU 100.

The light emitting element drive circuit 73 controls the amount of light emission of the light emitting element 71, according to a command signal from the CPU 100.

The arterial volume detection circuit 74 outputs, to the CPU 100, a volume pulse wave signal (arterial volume signal PGdc) based on the amount of transmitted or reflected light in the absorption band of hemoglobin included in blood (red blood cells) flowing through the blood vessels that reaches the light receiving element 72 after being emitted by the light emitting element 71, and an arterial volume change signal PGac of the AC component of the volume pulse wave signal which is obtained by processing the volume pulse wave signal with a high-pass filter (HPF) circuit. For example, a signal exceeding 0.6 Hz is taken as the AC component, assuming a filter constant of the HPF circuit of 0.6 Hz.

The pressure sensor 32 is a capacitance pressure sensor, and the volume value changes due to cuff pressure. The oscillation circuit 33 outputs an oscillation frequency signal that depends on the volume value of the pressure sensor 32 to the CPU 100. The CPU 100 detects pressure by converting the signal obtained from the oscillation circuit 33 into pressure.

Figure 4:
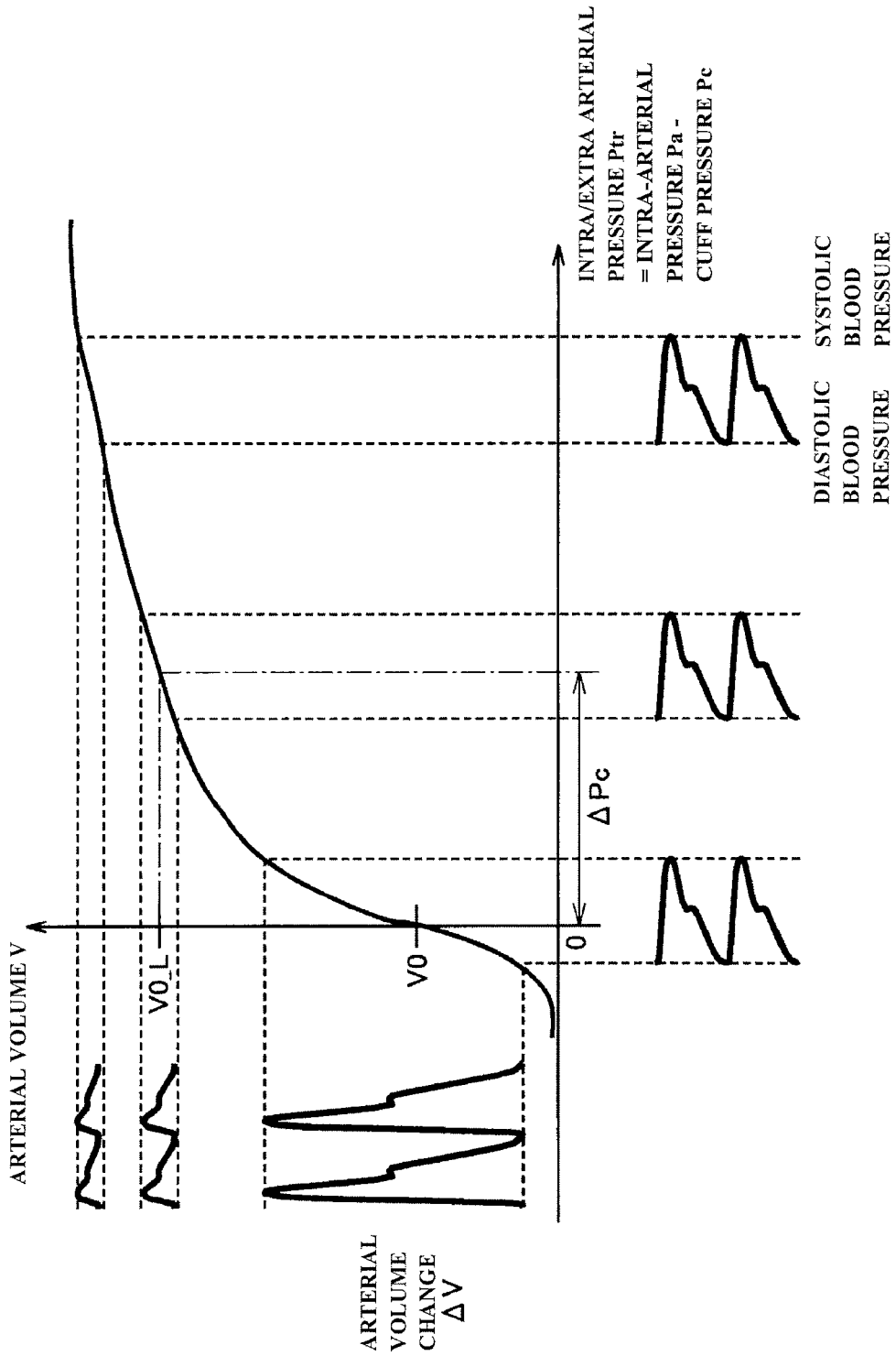
FIG. 4 is a graph showing mechanical properties of an artery.

FIG. 4 is a graph showing the mechanical properties of an artery. The graph in FIG. 4 shows the relationship between intra/extra-arterial pressure difference Ptr and arterial volume V, with intra/extra-arterial pressure difference Ptr shown on the horizontal axis and arterial volume V shown on the vertical axis. Intra/extra-arterial pressure difference Ptr indicates the difference between an intra-arterial pressure Pa and a cuff pressure (external pressure on body) Pc that is applied from outside the body by the cuff.

As shown in this graph, the mechanical properties of an artery generally show strong nonlinearity. When the intra/extra-arterial pressure difference Ptr is 0 (equilibrium state), that is, when the arterial wall is in an unloaded state, the compliance (amount of change in volume due to pulse) of the artery will be maximized. In other words, the trackability (developability) of volume change relative to pressure change will be maximized.

With a typical volume compensation method, blood pressure is measured by sequentially controlling external pressure on the body (cuff pressure), such that the detected arterial volume will always equal a volume value V0 at the point in time at which the intra/extra-arterial pressure difference Ptr is 0. Thus, the volume value, or control target value, V0 at the point in time at which of the intra/extra-arterial pressure difference Ptr is 0 needs to be determined before measuring blood pressure.

Figure 5:
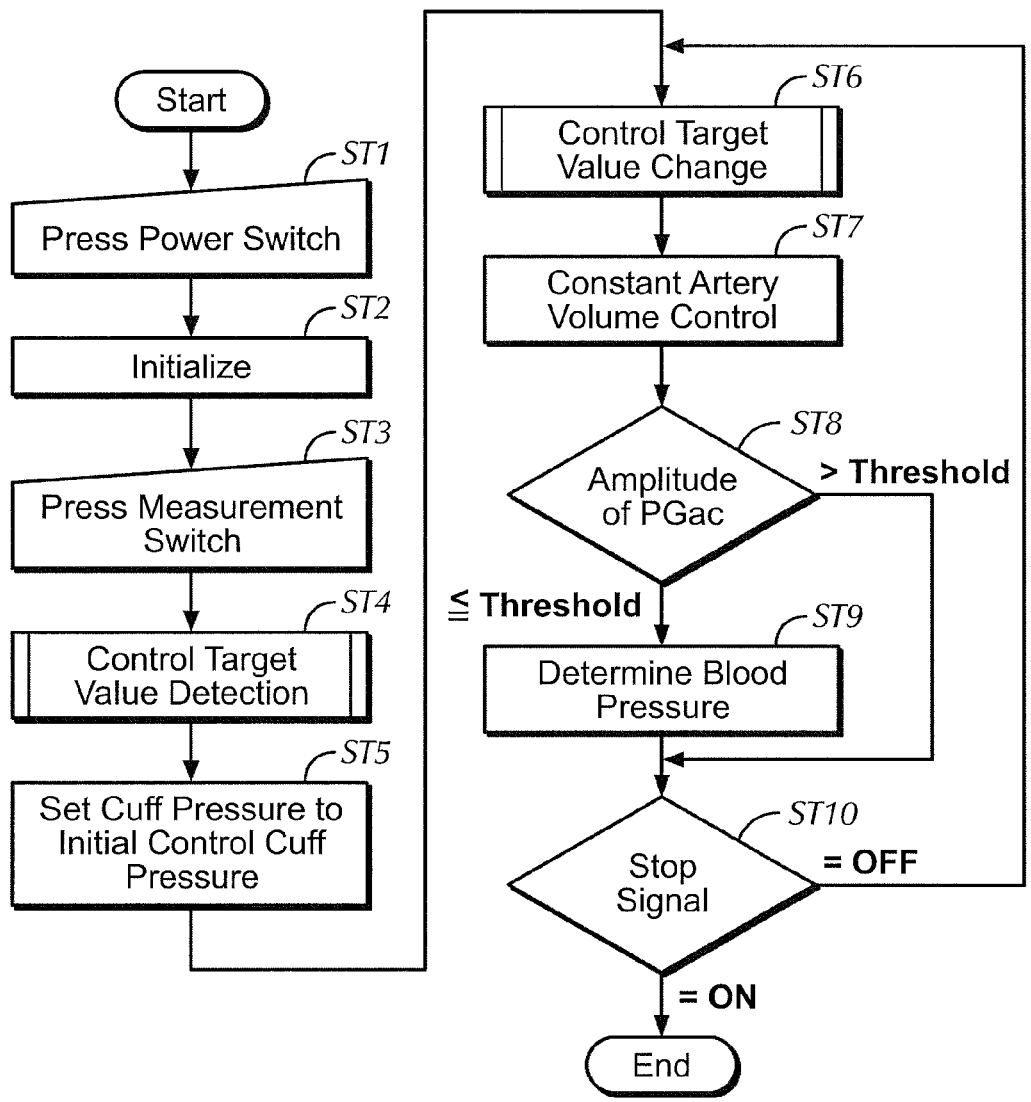
FIG. 5 is a flowchart showing the flow of blood pressure measurement processing in an embodiment of the present invention.

FIG. 5 is a flowchart showing the flow of blood pressure measurement processing in an embodiment of the present invention. Referring to FIG. 5, first, the CPU 100 waits for input of an operation in which the power switch 41A is pressed (step ST1).

When the power switch 41A has been pressed, the CPU 100 performs initialization processing (step ST2). Specifically, the CPU 100, as initialization processing, initializes the memory area of the memory unit 42 used for this processing, exhausts the air in the air bag 21, and performs 0 mm Hg correction of the pressure sensor 32.

Next, the CPU 100 waits for input of an operation in which the measurement switch 41B is pressed (step ST3). When the measurement switch 41B has been pressed, the CPU 100 executes control target value detection processing (step ST4).

Figure 6:
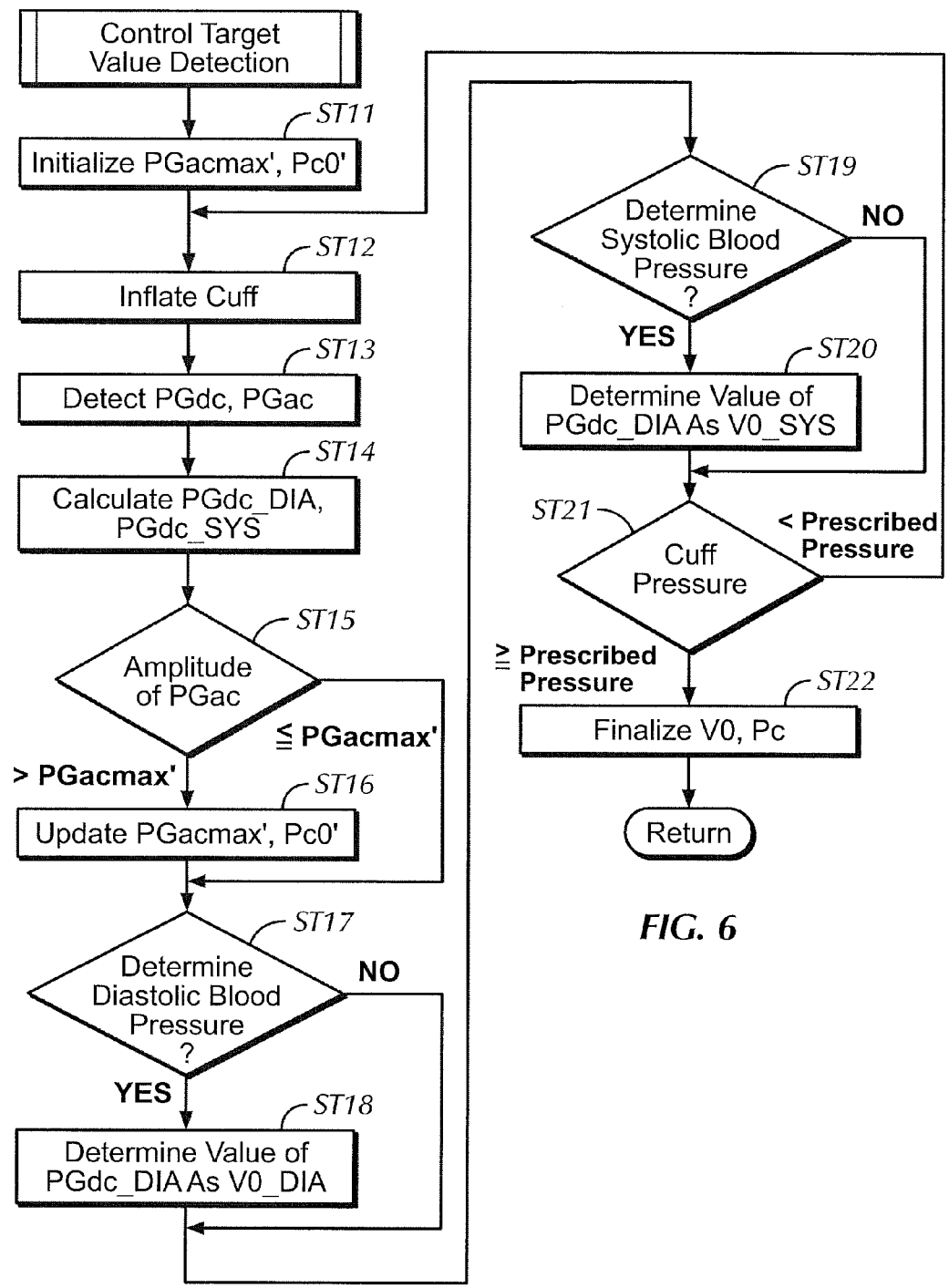
FIG. 6 is a flowchart showing the flow of control target value detection processing in an embodiment of the present invention.

FIG. 6 is a flowchart showing the flow of control target value detection processing in an embodiment of the present invention. Referring to FIG. 6, first, the CPU 100 initializes a maximum value PGacmax' of the arterial volume change signal and a cuff pressure value Pc0' that are stored in the memory unit 42 (step ST11). Note that because the maximum value PGacmax' of the arterial volume change signal and the cuff pressure value Pc0' are updated as needed in the following processing, these values are provisional values until they are ultimately finalized.

Next, the CPU 100 controls the drive of the pump drive circuit 53 to increase the cuff pressure (step ST12). At the stage of increasing the cuff pressure, the CPU 100 detects the signals (arterial volume signal PGdc, arterial volume change signal PGac) output from the arterial volume detection circuit 74 (step ST13).

Figure 7:
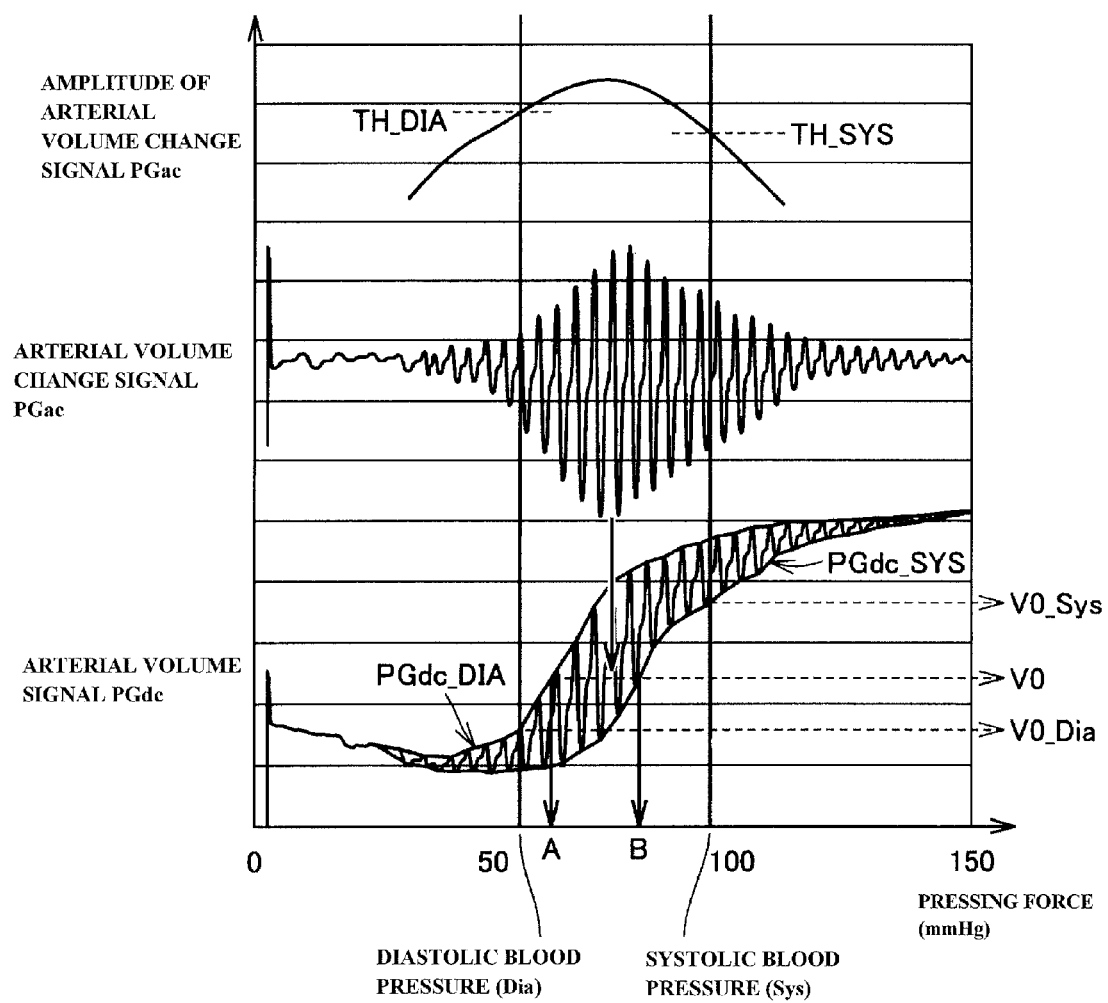
FIG. 7 is a graph for illustrating a method of determining a control target value in an embodiment of the present invention.

FIG. 7 is a graph for illustrating a method of determining a control target value in an embodiment of the present invention. Referring to FIG. 7, the graph on the third level that increases in response to an increase in pressing force (cuff pressure) while oscillating slightly up and down shows the arterial volume signal PGdc. Also, the graph on the second level shows the arterial volume change signal PGac.

Returning to FIG. 6, the maximum point of the amplitude of the arterial volume signal PGdc is detected per heartbeat cycle, and the maximum points are interpolated using an arbitrary curve (here, a straight line). This curve connects the values of the arterial volume signal at the point in time of diastolic blood pressure per heartbeat. Let this curve be PGdc_DIA. Also, the minimum point of the amplitude of the arterial volume signal PGdc is detected per heartbeat cycle, and the minimum points are interpolated using an arbitrary curve (here, a straight line). This curve connects the arterial volume values at the point in time of systolic blood pressure per heartbeat. Let this curve be PGdc_SYS. In this way, the CPU 100 calculates the curves PGdc_DIA and PGdc_SYS (step ST14).

Referring again to FIG. 7, the graphs on the third level above and below the graph of the arterial volume signal PGdc respectively show the curve PGdc_DIA and the curve PGdc_SYS.

Note that although linearly interpolated curves PGdc_DIA and PGdc_SYS are calculated here, one or more embodiments of the present invention are not limited thereto, and curves PGdc_DIA and PGdc_SYS interpolated with a spline curve may be calculated.

Returning to FIG. 6, the CPU 100 judges whether the amplitude of one heartbeat cycle of the arterial volume change signal PGac detected at step ST13 is greater than the maximum value PGacmax' of the amplitude of the arterial volume change signal PGac to date from the point at which cuff pressure starts to increase (step ST15). If judged to be greater, the CPU 100 updates the maximum value PGacmax' with the value of the amplitude at that time, and also updates the cuff pressure Pc0' at that time (step ST16).

Referring again to FIG. 7, the graph on the first level shows a line, or envelope, connecting the values of the amplitude of the arterial volume change signal PGac. When the maximum value PGacmax' of the amplitude of the arterial volume change signal has been determined, the CPU 100 calculates two thresholds TH_DIA and TH_SYS by multiplying the maximum value PGacmax' by prescribed constants (e.g., 0.7 and 0.5).

The CPU 100 then extrapolates, as the diastolic blood pressure (Dia), a cuff pressure at the point where the envelope intersects with the threshold TH_DIA on the side on which the cuff pressure is lower than a cuff pressure MEAN at the point in time where the maximum value PGacmax' was detected.

Also, the CPU 100 extrapolates, as the systolic blood pressure (Sys), a cuff pressure at the point where the envelope intersects with the threshold TH_SYS on the side on which the cuff pressure is higher than the cuff pressure MEAN. The method of determining systolic blood pressure and diastolic blood pressure in this way is called a volume-oscilloimetric method.

Returning to FIG. 6, the CPU 100 judges whether diastolic blood pressure has been determined using the volume-oscillometric method (step ST17). If it is judged that diastolic blood pressure has been determined, the CPU 100 determines the value of the curve PGdc_DIA calculated at step ST14 at the time of diastolic blood pressure as an arterial volume value V0_DIA at the time of diastolic blood pressure (step ST18).

Also, the CPU 100 judges whether systolic blood pressure has been determined using the volume-oscillometric method (step ST19). If it is judged that systolic blood pressure has been determined, the CPU 100 determines the value of the curve PGdc_SYS calculated at step ST14 at the time of systolic blood pressure as an arterial volume value V0_SYS at the time of systolic blood pressure (step ST20).

Referring again to FIG. 7, the value of the arterial volume signal PGdc at the point where a line indicating the diastolic blood pressure intersects with the curve PGdc_DIA is the arterial volume value V0_DIA at the time of diastolic blood pressure. Also, the value of the arterial volume signal PGdc at the point where a line indicating the systolic blood pressure intersects with the curve PGdc_SYS is the arterial volume value V0_SYS at the time of systolic blood pressure.

Returning to FIG. 6, the CPU 100 judges whether the cuff pressure has reached a prescribed pressure (step ST21). The prescribed pressure is a pressure sufficiently higher than the systolic blood pressure of the subject, such as 200 mm Hg, for example. If it is judged that the prescribed pressure has not been reached, the CPU 100 returns to the processing of step ST12 and repeats the processing until step ST20.

If it is judged that the cuff pressure has reached the prescribed pressure, the CPU 100 finalizes the maximum value PGacmax' of the amplitude of the arterial volume change signal, calculates the mean value of the arterial volume signal PGdc for one heartbeat cycle at the time that the maximum value PGacmax' was reached as an initial value V0 of the control target value, and finalizes the cuff pressure Pc0' at that time as an initial control cuff pressure Pc0 (step ST22). Thereafter, the CPU 100 returns to the processing from which this processing was originally called.

Returning to FIG. 5, the CPU 100 sets the cuff pressure to the initial control cuff pressure P0 finalized at step ST22 of FIG. 6 (step ST5). Next, the CPU 100 executes control target value change processing (step ST6). Note that when the control target value change processing is performed for the first time, the initial value V0 of the control target value determined at step ST22 of FIG. 6 is set as the control target value.

Figure 8:
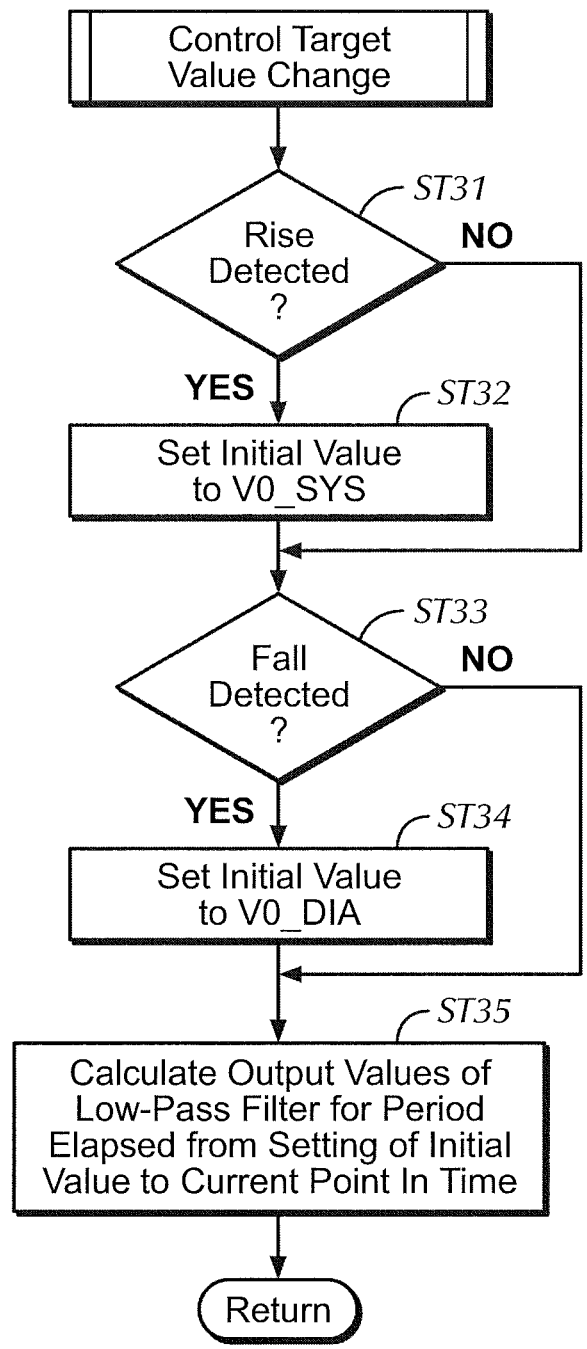
FIG. 8 is a flowchart showing the flow of control target value change processing in an embodiment of the present invention.

FIG. 8 is a flowchart showing the flow of control target value change processing in an embodiment of the present invention. Referring to FIG. 8, first, the CPU 100 judges whether a rising point of the arterial volume signal PGdc has been detected (step ST31).

Figure 9:
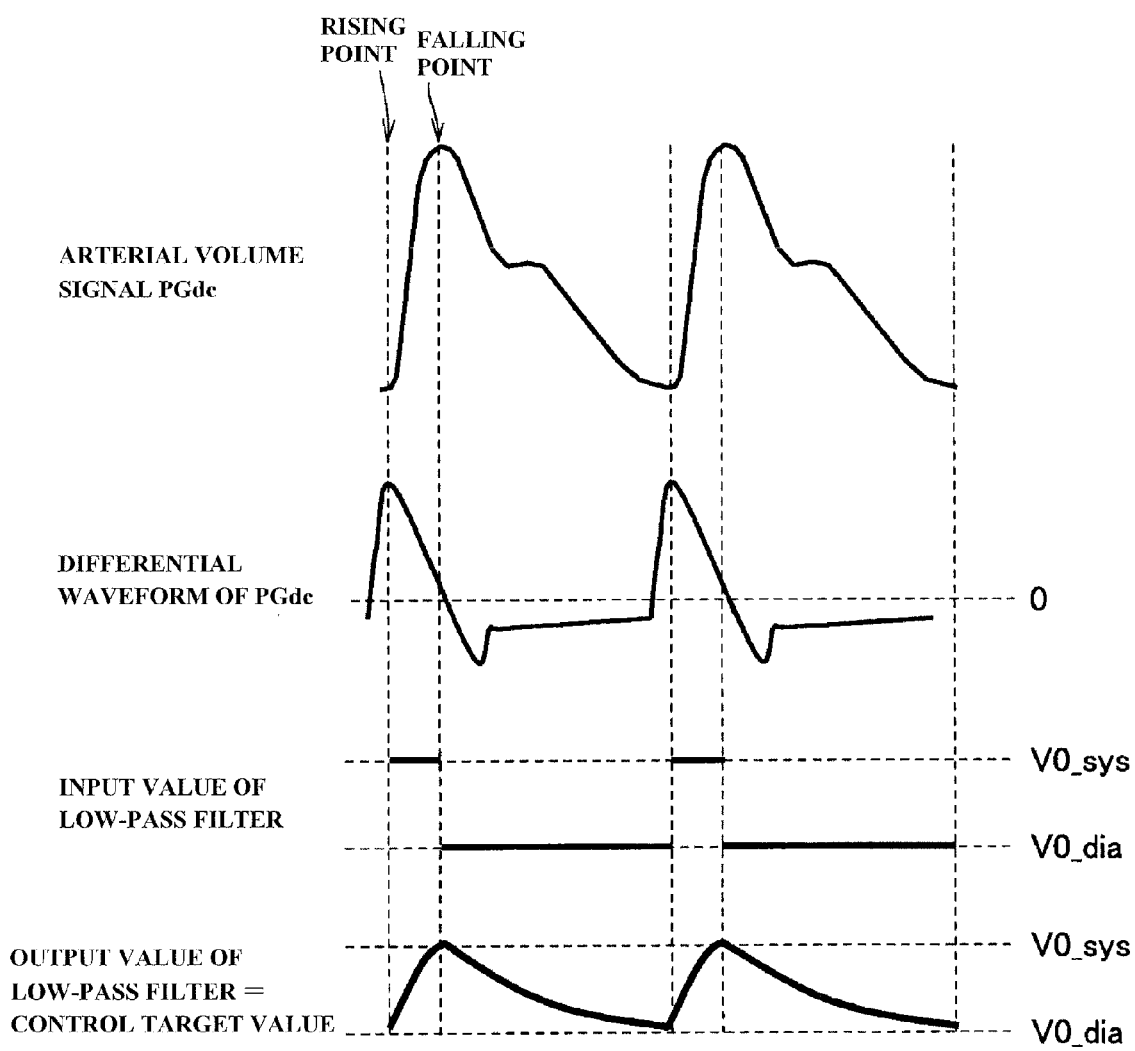
FIG. 9 is a graph for illustrating a method of changing a control target value in an embodiment of the present invention.

FIG. 9 is a graph for illustrating a method of changing the control target value in an embodiment of the present invention. Referring to FIG. 9, the CPU 100 calculates the differential waveform shown by the graph on the second level from the arterial volume signal PGdc shown by the graph on the first level. The CPU 100 then judges that a rising point of the arterial volume signal PGdc has been detected, when the maximum point (maxima) of one heartbeat cycle of the differential waveform shown by the graph on the second level is detected. The rising point is the minimum point (minima) of one heartbeat cycle of the arterial volume signal PGdc.

Returning to FIG. 8, if it is judged that a rising point of the arterial volume signal PGdc has been detected, the CPU 100 sets the initial value to the arterial volume value V0_SYS at the time of systolic blood pressure determined at step ST20 of FIG. 6 (step ST32).

Next, the CPU 100 judges whether a falling point of the arterial volume signal PGdc has been detected (step ST33).

Referring again to FIG. 9, the CPU 100 judges that a falling point of the arterial volume signal PGdc has been detected, when the point at which the values of one heartbeat cycle of the differential waveform shown by the graph on the second level change from plus to minus, is detected, or in other words, the point of a zero value (zero cross point) is detected. The falling point is the maximum point of one heartbeat cycle of the arterial volume signal PGdc.

Returning to FIG. 8, if it is judged that a falling point of the arterial volume signal PGdc has been detected, the CPU 100 sets an initial value to the arterial volume value V0_DIA at the time of diastolic blood pressure determined at step ST18 of FIG. 6 (step ST34).

Next, the CPU 100 calculates the output values of a low-pass filter (LPF) for the period elapsed from the setting of the initial value at step ST32 or step ST34 to the current point in time as control target values (step ST35). Thereafter, the CPU 100 returns to the processing from which this processing was originally called.

Specifically, during the fall time from the rising point to the falling point of the arterial volume signal, the CPU 100 calculates, as the control target value, a value output from a prescribed low-pass filter at the point in time when step ST35 is executed after time t has elapsed from the rising point, in the case where the arterial volume value V0_SYS at the time of systolic blood pressure is input to the prescribed low-pass filter. During the rise time from the falling point to the next rising point of the arterial volume signal, the CPU 100 calculates, as the control target value, a value output from the prescribed low-pass filter at the point in time when step ST35 is executed after time t has elapsed from the falling point, in the case where the arterial volume value V0_DIA at the time of diastolic blood pressure is input to the prescribed low-pass filter.

Referring again to FIG. 9, during the fall time of the arterial volume signal shown by the graph on the first level, the arterial volume value V0_DIA at the time of diastolic blood pressure is input to the prescribed low-pass filter as an input value, as shown by the graph on the third level. Output values that change smoothly from the arterial volume value V0_SYS at the time of systolic blood pressure to a vicinity of the arterial volume value V0_DIA at the time of diastolic blood pressure, such as shown by the graph on the fourth level, are thereby output from the prescribed low-pass filter.

Also, during the rise time of the arterial volume signal shown by the graph on the first level, the arterial volume value V0_SYS at the time of systolic blood pressure is input to the prescribed low-pass filter as an input value, as shown by the graph on the third level. Output values that change smoothly from the arterial volume value V0_DIA at the time of diastolic blood pressure to a vicinity of the arterial volume value V0_SYS at the time of systolic blood pressure, such as shown by the graph on the fourth level, are thereby output from the prescribed low-pass filter.

The output values of the prescribed low-pass filter during an elapsed time t from the rising point or the falling point to the point in time at which step ST35 is executed are calculated as control target values.

Note that the cutoff frequency or time constant of the prescribed low-pass filter need only respectively be set to, for example, about 5 Hz or 0.03 seconds during the rise time and about 1 Hz or 0.16 seconds during the fall time. Here, with regard to variations in blood pressure, because the fall time is longer than the rise time, the time constant of the prescribed low-pass filter for calculating the control target value is also set longer for the fall time than for the rise time of the arterial volume signal PGdc.

Returning to FIG. 5, the CPU 100, as constant arterial volume control, controls the pump drive circuit 53 and the valve drive circuit 54 to change the cuff pressure Pc, such that the value of the arterial volume signal PGdc matches the control target value (step ST7).

The CPU 100 judges whether the amplitude of the arterial volume change signal PGac is less than or equal to a prescribed threshold (step ST8). Because an amplitude at or below the prescribed threshold indicates that constant arterial volume control is convergent, the CPU 100 determines the cuff pressure Pc at that time as the blood pressure of the subject, and displays the determined blood pressure value on the display unit 40 (step ST9). The determined blood pressure value may be stored in the flash memory 43.

The CPU 100 then judges whether a stop signal has been input as a result of the stop switch 41C being operated (switch in ON state). If it is judged that a stop signal has not been input (switch in OFF state), the CPU 100 returns to the processing of step ST6. On the other hand, if it is judged that a stop signal has been input (switch in ON state), the CPU 100 ends the blood pressure measurement processing, and turns off power to the electronic sphygmomanometer 1.

In the case where a fixed control target value V0 is used such as with blood pressure measurement using a conventional volume compensation method, the mean value of the arterial volume signal PGdc for one heartbeat cycle when the amplitude of the arterial volume change signal PGac is maximized is derived as the control target value V0, with reference to FIG. 7.

In the case where this fixed control target value V0 is used, the value of diastolic blood pressure is calculated as a value A, which is the value of the arterial volume signal PGdc at the intersection of the line of V0 and the curve PGdc_DIA, and the value of systolic blood pressure is calculated as a value B, which is the value of the arterial volume signal PGdc at the intersection of the line of V0 and the curve PGdc_SYS.

In the case where the fixed control target value V0 is used, an error thus occurs between the calculated values and the true blood pressure values. In this way, the value of the arterial volume signal PGdc will change more than actual change in arterial volume under the influence of mechanical hysteresis of the artery and the deformation of body tissue around the artery in the process of compressing the artery.

In the case where constant arterial volume control is performed by changing the arterial volume value V0_DIA at the time of diastolic blood pressure and the arterial volume value V0_SYS at the time of systolic blood pressure, as in the present embodiment, error around the diastolic blood pressure and the systolic blood pressure can be lessened, because the values obtained as the diastolic blood pressure and the systolic blood pressure of the subject are values close to the true blood pressure values.

Furthermore, because control target values obtained by smoothly interpolating the arterial volume value V0_DIA at the time of diastolic blood pressure and the arterial volume value V0_SYS at the time of systolic blood pressure are used, pseudo reproduction of the control target values at all points in time during one heartbeat can be carried out, enabling continuous blood pressure to be calculated with little error, not only around the diastolic blood pressure and the systolic blood pressure.

Next, variations of the abovementioned embodiment will be described.

(1) In the aforementioned embodiment, the input values form a pulse signal in which the arterial volume value V0_SYS at the time of systolic blood pressure serves as the input value to the prescribed low-pass filter from the rising point to the falling point of the arterial volume signal, and the arterial volume value V0_DIA at the time of diastolic blood pressure serves as the input value from the falling point to the next rising point of the arterial volume signal.

However, one or more embodiments of the present invention are not limited thereto, and any input value that enables output values to be obtained from a prescribed low-pass filter, such that the output values change smoothly from the arterial volume value V0_DIA at the time of diastolic blood pressure to a vicinity of the arterial volume value V0_SYS at the time of systolic blood pressure, between the rising point and the falling point, and change smoothly from the arterial volume value V0_SYS at the time of systolic blood pressure to a vicinity of the arterial volume value V0_DIA at the time of diastolic blood pressure, between the falling point and the next rising point, may be used.

(2) In the aforementioned embodiment, the cutoff frequencies and time constants of the low-pass filter are respectively fixed by the rise time and fall time of the arterial volume signal PGdc.

However, one or more embodiments of the present invention are not limited thereto, and a configuration may be adopted in which an outline of the heartbeat cycle of the subject is provisionally measured when the electronic sphygmomanometer 1 is activated, the cutoff frequencies or time constants for the rise time and fall time are respectively calculated from the time required to rise during the heartbeat cycle and the time required to fall during the heartbeat cycle, and the calculated cutoff frequencies or time constants are used.

Because the control target value can thereby be changed according to the heartbeat cycle of each subject, more precise blood pressure measurement can be performed according to the subject.

(3) In the aforementioned embodiment, the cutoff frequencies and time constants of the low-pass filter are respectively fixed by the rise time and fall time of the arterial volume signal PGdc. The heartbeat cycle changes, but no rapid change occurs. Thus, even if the cutoff frequencies and time constants are fixed, significant error does not arise in blood pressure measurement.

However, one or more embodiments of the present invention are not limited thereto, and a configuration may be adopted in which the cutoff frequencies or time constants for the rise time and fall time are changed every one heartbeat cycle or every plurality of heartbeat cycles.

For example, a configuration may be adopted in which the cutoff frequencies or time constants for the rise time and the fall time are calculated, according to the time required to rise during a heartbeat cycle that is one heartbeat cycle previous or a plurality of heartbeat cycles previous, and the calculated cutoff frequencies or time constants are used during that heartbeat cycle or during a plurality of heartbeat cycles from that heartbeat cycle.

Because the control target value can be changed during continuous blood pressure measurement according to the heartbeat cycle, even in the case where the heartbeat cycle changes in some way, more precise continuous blood pressure measurement can be performed, according to the change in the heartbeat cycle.

(4) In the aforementioned embodiment, in order to smoothly change the control target value at the rising point and the falling point, the output value of a prescribed low-pass filter that smoothly interpolates between the arterial volume value V0_DIA at the time of diastolic blood pressure and the arterial volume value V0_SYS at the time of systolic blood pressure were used as control target values. However, one or more embodiments of the present invention are not limited thereto, and any method of interpolating smoothly between the arterial volume value V0_DIA at the time of diastolic blood pressure and the arterial volume value V0_SYS at the time of systolic blood pressure may be used, such as interpolating with a different curve to an output curve of a low-pass filter, like a sine wave, or interpolating linearly, like a triangular wave or a saw-tooth wave.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 electronic sphygmomanometer
10 main body
20 cuff
21 air bag
30 air system
31 air tube
32 pressure sensor
33 oscillation circuit
40 display unit
41 operation unit
41A power switch
41B measurement switch
41C stop switch
41D memory switch
41E ID switch
42 memory unit
43 flash memory
44 power source
45 timer
50 adjustment mechanism
51 pump
52 valve
53 pump drive circuit
54 valve drive circuit
70 arterial volume sensor
71 light emitting element
72 light receiving element
73 light emitting element drive circuit
74 arterial volume detection circuit
100 CPU

The invention claimed is:

1. A blood pressure measurement device for measuring blood pressure in accordance with a volume compensation method, comprising:
   a cuff that is configured to fit on a blood pressure measurement site to compress an artery of the measurement site;
   an inflation/deflation unit that increases and decreases a pressure inside the cuff;
   a pressure detection unit that detects a cuff pressure, which is the pressure inside the cuff;
   a volume detection unit that detects an arterial volume signal indicating a volume of the artery per unit length; and
   a control unit comprising:
      pressure control means for adjusting the pressure of the cuff by controlling the inflation/deflation unit, such that the volume indicated by the arterial volume signal detected by the volume detection unit matches a prescribed control target value; and
      extraction means for extracting, as a blood pressure of a subject, the cuff pressure detected by the pressure detection unit when a prescribed condition for judging that the volume matches the prescribed control target value as a result of adjustment by the pressure control means is satisfied,
      wherein the control unit further comprises:
         determination means for respectively determining, as a value at a time of diastolic blood pressure and a value at a time of systolic blood pressure, values of the arterial volume signal detected by the volume detection unit when the cuff pressure matches a diastolic blood pressure and a systolic blood pressure calculated with a prescribed method;
         change point detection means for detecting a rising point where the volume indicated by the arterial volume signal detected by the volume detection unit starts to increase and a falling point where the volume starts to decrease; and
         change means for changing the prescribed control target value from the value at the time of diastolic blood pressure determined by the determination means to a vicinity of the value at the time of systolic blood pressure, during a rise time from when the rising point is detected by the change point detection means until when the falling point is detected, and changing the prescribed control target value from the value at the time of systolic blood pressure determined by the determination means to a vicinity of the value at the time of diastolic blood pressure, during a fall time from when the falling point is detected until when the rising point is detected.

2. The blood pressure measurement device according to claim 1, wherein the change means, during the rise time, changes the prescribed control target value in accordance with a value output when a waveform that is stepped from the value at the time of diastolic blood pressure determined by the determination means to the value at the time of systolic blood pressure is input to a low-pass filter, and, during the fall time, changes the prescribed control target value in accordance with a value output when a waveform that is stepped from the value at the time of systolic blood pressure to the value at the time of diastolic blood pressure is input to the low-pass filter.

3. The blood pressure measurement device according to claim 2, wherein a time constant of the low-pass filter is set longer for the fall time than for the rise time.

4. A control method of controlling a blood pressure measurement device that is for measuring blood pressure in accordance with a volume compensation method and includes a cuff that compresses an artery of a blood pressure measurement site in a case where the device is fitted on the measurement site, an inflation/deflation unit that increases and decreases a pressure inside the cuff, a pressure detection unit that detects a cuff pressure, which is the pressure inside the cuff, a volume detection unit that detects an arterial volume signal indicating a volume of the artery per unit length, and a control unit, the control method comprising:
   a step of the control unit respectively determining, as a value at a time of diastolic blood pressure and a value at a time of systolic blood pressure, values of the arterial volume signal detected by the volume detection unit when the cuff pressure matches a diastolic blood pressure and a systolic blood pressure calculated with a prescribed method;
   a step of the control unit detecting a rising point where the volume indicated by the arterial volume signal detected by the volume detection unit starts to increase and a falling point where the volume starts to decrease;
   a step of the control unit changing a prescribed control target value from the determined value at the time of diastolic blood pressure to a vicinity of the value at the time of systolic blood pressure, during a rise time from when the rising point is detected until when the falling point is detected, and changing the prescribed control target value from the determined value at the time of systolic blood pressure to a vicinity of the value at the time of diastolic blood pressure, during a fall time from when the falling point is detected until when the rising point is detected;

a step of the control unit adjusting the pressure of the cuff by controlling the inflation/deflation unit, such that the volume indicated by the arterial volume signal detected by the volume detection unit matches the prescribed control target value; and a step of the control unit extracting, as a blood pressure of a subject, the cuff pressure detected by the pressure detection unit when a prescribed condition for judging that the volume matches the prescribed control target value as a result of adjustment of the pressure of the cuff is satisfied.

* * * * *